(12) United States Patent
Taylor et al.

(10) Patent No.: US 11,458,104 B1
(45) Date of Patent: *Oct. 4, 2022

(54) ENTERIC COATED TIOPRONIN TABLET

(71) Applicant: Mission Pharmacal Company, San Antonio, TX (US)

(72) Inventors: Jon Taylor, San Antonio, TX (US); Stuart Smoot, San Antonio, TX (US); Stuart Schoenherr, Spring Branch, TX (US); Paul Werchan, Bulverde, TX (US)

(73) Assignee: MISSION PHARMACAL COMPANY, San Antonio, TX (US)

( * ) Notice: Subject to any disclaimer, the term of this patent is extended or adjusted under 35 U.S.C. 154(b) by 146 days.

This patent is subject to a terminal disclaimer.

(21) Appl. No.: 16/562,224

(22) Filed: Sep. 5, 2019

Related U.S. Application Data

(63) Continuation of application No. 16/014,669, filed on Jun. 21, 2018, now abandoned.

(51) Int. Cl.
*A61K 9/28* (2006.01)
*A61K 31/198* (2006.01)
*A61K 9/20* (2006.01)

(52) U.S. Cl.
CPC .......... *A61K 9/2866* (2013.01); *A61K 9/2846* (2013.01); *A61K 9/2886* (2013.01); *A61K 31/198* (2013.01); *A61K 9/2086* (2013.01)

(58) Field of Classification Search
None
See application file for complete search history.

(56) References Cited

U.S. PATENT DOCUMENTS

| | | | | |
|---|---|---|---|---|
| 2,993,837 A * | 7/1961 | Millar | ..................... | A61K 9/284 |
| | | | | 424/482 |
| 5,225,202 A | 7/1993 | Hodges et al. | | |
| 6,368,628 B1 * | 4/2002 | Seth | ..................... | A61K 9/2813 |
| | | | | 424/480 |
| 7,645,460 B2 * | 1/2010 | Dansereau | ............... | A61P 19/10 |
| | | | | 424/474 |
| 9,642,809 B2 | 5/2017 | Hemmingsen et al. | | |
| 9,795,576 B2 * | 10/2017 | Kolter | .................. | A61K 9/5073 |
| 9,867,779 B2 | 1/2018 | Zhao et al. | | |
| 2006/0134216 A1 | 6/2006 | Farrell et al. | | |
| 2007/0196399 A1 * | 8/2007 | Kusaki | .................. | A61K 9/5026 |
| | | | | 424/400 |
| 2010/0310541 A1 | 12/2010 | Kessler et al. | | |
| 2017/0246176 A1 | 8/2017 | Tsubota | | |
| 2019/0282525 A1 | 9/2019 | Chetlapalli | | |

FOREIGN PATENT DOCUMENTS

| | | | | |
|---|---|---|---|---|
| CN | 1698594 A | 11/2005 | | |
| CN | 1887859 A | 1/2007 | | |
| CN | 101045044 A | 10/2007 | | |
| CN | 101062084 A | 10/2007 | | |
| CN | 101590026 A | 12/2009 | | |
| CN | 102697750 A | 10/2012 | | |
| CN | 103705482 A | 4/2014 | | |
| EP | 1681052 A1 * | 7/2006 | ......... | A61K 31/4439 |
| GB | 2352172 A * | 1/2001 | .......... | A61K 9/2866 |
| WO | WO-9737641 A1 * | 10/1997 | .......... | A61K 9/2866 |
| WO | WO-9937290 A1 * | 7/1999 | .......... | A61K 9/2846 |
| WO | 2012/006959 A1 | 1/2012 | | |
| WO | 2016/140933 A2 | 9/2016 | | |
| WO | 2017/161318 A1 | 9/2017 | | |
| WO | 2018/232407 A1 | 12/2018 | | |

OTHER PUBLICATIONS

Kuhar et al. "Evaluation of Selected New Drugs: 1988," AAOHN Journal 37(10):428-433, 1989.*
ShinEtsu "Pharmacoat®" accessed 2020 ; https://www.metolose.jp/en/pharmaceutical/tc-5.html.*
Tanno et al. "A novel oral dosage form that reduces food-drug interactions responsible for low drug absorption in the fed state: utlizaton of enteric coating agents that start to dissolve at higher pH," Drug Delivery System 25(4):384-391, 2010, abstract only (Year: 2010).*
Tanno et al. "Site-specific drug delivery to the middle-to-lower region of the small intestine reduces food-drug interactions that are responsible for low drug absorption in the fed state," Journal of Pharmaceutical Sciences 97(12):5341-5353, 2008 (Year: 2008).*
Huang et al. "Preparation and dissolution of tiopronin enteric capsules," Yiyao Daobao 25(9):948-949, 2006, abstract only (Year: 2006).*
Package Leaflet for "Bisacodyl 5mg Tablets," last revised Jun. 2016 (4 pages).
Perrett, "The Metabolism and Pharmacology of D-Penicillamine in Man," *The Journal of Rheumatology* Supplement No. 7 8:41-50, 1981.
ShinEtsu "Pharmacoat®," printed 2019, available at http://www.metolose.jp/en/pharmaceutical/tc-5.html (2 pages).

(Continued)

*Primary Examiner* — David J Blanchard
*Assistant Examiner* — Alissa Prosser
(74) *Attorney, Agent, or Firm* — Seed IP Law Group LLP

(57) ABSTRACT

A solid pharmaceutical composition is provided that includes a core, an inner coating, and an outer coating. The core includes tiopronin as an active agent. Further, the inner coating, which includes a cellulose-based polymer, surrounds the core, and the outer coating, which includes an enteric polymer, surrounds the inner coating. As a result of the specific components of the solid pharmaceutical composition, the solid pharmaceutical composition exhibits a fed state $C_{max}$ of tiopronin that is at least 70% of a 12-hour fasted state $C_{max}$ of tiopronin after oral administration of the solid pharmaceutical composition when administered as a 300 milligram dose. As such, it is possible for the solid pharmaceutical composition to be administered orally with or without food (e.g., in a fed or fasted state) while still achieving a desired maximum plasma concentration of the tiopronin in a delayed release formulation.

6 Claims, 4 Drawing Sheets

(56) References Cited

OTHER PUBLICATIONS

THIOLA® (Tiopronin) Tablet formulation, revised Nov. 2012, available at https://dailymed.nlm.nih.gov/dailymed/fda/fdaDrugXsl.cfm?setid=494a714e-923c-cd57-df6c-12886afb265a&type=display (7 pages).

* cited by examiner

ENTERIC COATED TIOPRONIN TABLET

BACKGROUND OF THE INVENTION

Cystinuria is an autosomal recessive disease that is characterized by high concentrations of the amino acid cysteine in the urine. Cysteine tends to form cysteine-cysteine dimers, called cystine, through disulfide bonding. Cystine exhibits poor aqueous solubility and high levels in urine lead to the formation of cystine stones in the kidneys, ureter, and bladder. Cystine stones frequently reoccur and are typically larger than other kidney stones. The disease, which affects about 1 in 7,000 people worldwide, is inherited and is passed down from a parent to a child due to a genetic defect. Symptoms of cystinuria can include pain while urinating, blood in the urine, sharp pain in the side or back, pain near the groin, pelvis, or abdomen, nausea, vomiting, or a combination thereof.

Unfortunately, there is no cure for cystinuria, as it is a lifelong condition that requires careful monitoring and treatment. Patients must have active monitoring of their urine cystine levels to prevent stones from forming. Treatment involves conservative measures of high fluid intake, dietary modifications, and urinary alkalinization. In many cases conservative measures are not sufficient to prevent cystine stones from forming. Therefore, in these instances, the disease can be treated with a drug called tiopronin. Tiopronin is an acylated sulfhydryl-containing derivative of glycine with reducing and complexing properties. Tiopronin breaks the disulfide bond of cystine and binds the sulfhydryl group of the resultant cysteine monomers to form a soluble tiopronin-cysteine-mixed disulfide. Tiopronin-cysteine is more water-soluble than cystine and is readily excreted. This leads to a reduction in the urinary cystine concentration and subsequently reduces cystine stone formation. Tiopronin tablets are currently available under the brand name THIOLA®. The immediate-release tablet is sugar-coated and contains calcium carbonate, carnauba wax, ethyl cellulose, EUDRAGIT® E 100 (a cationic copolymer comprised of dimethylaminoethyl methacrylate, butyl methacrylate, and methyl methacrylate), hydroxypropyl cellulose, lactose, magnesium stearate, povidone, sugar, talc, and titanium dioxide. THIOLA® is typically taken three times per day.

However, the current tiopronin tablet formulation, like the only other medication approved for the treatment of cystinuria, d-penicillamine, should be taken on an empty stomach. The FDA approved prescribing information for THIOLA® states: "Whenever possible, THIOLA® should be given in divided doses 3 times/day at least one hour before or 2 hours after meals." THIOLA® should be taken on an empty stomach because tiopronin is a chelating agent. It has been shown that when d-penicillamine, a similar chelating agent, is taken with food rather than on an empty stomach, it can result in up to a 50% decrease in drug efficacy due to chelation of the drug with metals present in food.

Further, patients on tiopronin therapy often are prescribed an alkalinizing agent (e.g., potassium citrate), which must be taken with food and up to three times daily. Many patients therefore are required to take THIOLA® three times daily on an empty stomach, and an alkalinizing agent three times daily with food. This complicated and inconvenient dosing regimen is believed to reduce patient compliance and thereby increase the risk of cystine stone formation.

In addition, some patients taking THIOLA® have complained of sulfur-like eructation (burping) and nausea, which is potentially caused by dissolution of the immediate release sugar-coated tablet in the stomach.

As such, a need exists for an oral tiopronin pharmaceutical composition that can be taken with food. Additionally, a pharmaceutical composition that allows for the location of the dissolution of the composition to be altered (e.g., dissolution in the intestine rather than the stomach) to reduce the risk of eructation and nausea would be beneficial.

SUMMARY OF THE INVENTION

In accordance with one particular embodiment of the present invention, a solid pharmaceutical composition is disclosed. The composition includes a core comprising tiopronin; an inner coating surrounding the core, wherein the inner coating comprises a cellulose-based polymer; and an outer coating surrounding the inner coating. Further, the outer coating can include an enteric polymer, which helps to prevent the disintegration or dissolution of the composition in the gastric environment. As a result of the various components included in the solid pharmaceutical composition, the solid pharmaceutical composition exhibits a fed state $C_{max}$ of tiopronin that is at least 70% of a 12-hour fasted state $C_{max}$ of tiopronin after oral administration of a 300 milligram dose of the solid pharmaceutical composition.

In another embodiment, tiopronin can be present in an amount ranging from about 35 wt. % to about 75 wt. % based on the total weight of the solid pharmaceutical composition.

In still another embodiment, the core can further include a diluent, a binder, a disintegrant, a lubricant, or a combination thereof. Further, the diluent can be present in an amount ranging from about 10 wt. % to about 50 wt. % based on the total weight of the solid pharmaceutical composition. In addition, the binder can be present in an amount ranging from about 0.25 wt. % to about 3 wt. % based on the total weight of the solid pharmaceutical composition. Moreover, the disintegrant can be present in an amount ranging from about 1 wt. % to about 10 wt. % based on the total weight of the solid pharmaceutical composition. Further, the lubricant can be present in an amount ranging from about 0.25 wt. % to about 3 wt. % based on the total weight of the solid pharmaceutical composition.

In yet another embodiment, the cellulose-based polymer in the inner coating can be present in an amount ranging from about 0.5 wt. % to about 10 wt. % based on the total weight of the solid pharmaceutical composition.

In one more embodiment, the enteric polymer can be present in an amount ranging from about 0.25 wt. % to about 6 wt. % based on the total weight of the solid pharmaceutical composition.

In an additional embodiment, the enteric polymer can include an anionic methacrylic acid and ethyl acrylate copolymer.

In another embodiment, the outer coating can further include an anti-tacking agent and a plasticizer. Further, the anti-tacking agent can be present in an amount ranging from about 0.1 wt. % to about 4 wt. % based on the total weight of the solid pharmaceutical composition, while the plasticizer can be present in an amount ranging from about 0.025 wt. % to about 1 wt. % based on the total weight of the solid pharmaceutical composition.

In still another embodiment, the solid pharmaceutical composition can be in a form of a tablet, pill, or capsule.

In yet another embodiment, the fed state $C_{max}$ of tiopronin can range from about 2000 nanograms/milliliter to about 10,500 nanograms per milliliter after oral administration of a 300 milligram dose of the solid pharmaceutical composition.

In one more embodiment, a fed state $T_{max}$ of tiopronin can range from about 2.5 hours to about 6.5 hours after oral administration of a 300 milligram dose of the solid pharmaceutical composition and a 12-hour fasted state $T_{max}$ of tiopronin can range from about 1 hour to about 4.5 hours after oral administration of a 300 milligram dose of the solid pharmaceutical composition.

In an additional embodiment, a fed state $AUC_{0-\infty}$ of tiopronin can range from about 16,000 hours*nanograms/milliliter to about 48,000 hours*nanograms/milliliter after oral administration of a 300 milligram dose of the solid pharmaceutical composition and a 12-hour fasted state $AUC_{0-\infty}$ of tiopronin can range from about 20,000 hours*nanograms/milliliter to about 64,000 hours*nanograms/milliliter after oral administration of a 300 milligram dose of the solid pharmaceutical composition.

In another embodiment, a fed state $AUC_{0-t}$ of tiopronin can range from about 12,000 hours*nanograms/milliliter to about 40,000 hours*nanograms/milliliter after oral administration of a 300 milligram dose of the solid pharmaceutical composition and a 12-hour fasted state $AUC_{0-t}$ of tiopronin can range from about 16,000 hours*nanograms/milliliter to about 54,000 hours*nanograms/milliliter after oral administration of a 300 milligram dose of the solid pharmaceutical composition.

In still another embodiment, an amount of tiopronin present in the solid pharmaceutical composition after storage at 40° C. and a relative humidity of 75% for 6 months is at least 90% of an amount of tiopronin present in the solid pharmaceutical composition prior to storage, and wherein an amount of tiopronin present in the solid pharmaceutical composition after storage at 25° C. and a relative humidity of 60% for 9 months is at least 90% of an amount of tiopronin present in the solid pharmaceutical composition prior to storage.

In yet another embodiment, the solid pharmaceutical formulation can exhibit less than 10% dissolution when exposed to a 0.1 N HCl solution for 120 minutes and greater than 70% dissolution when exposed to a phosphate buffer solution having a pH of 6.8 for 45 minutes.

Other features and aspects of the present invention are set forth in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figure, in which.

Figure 1:
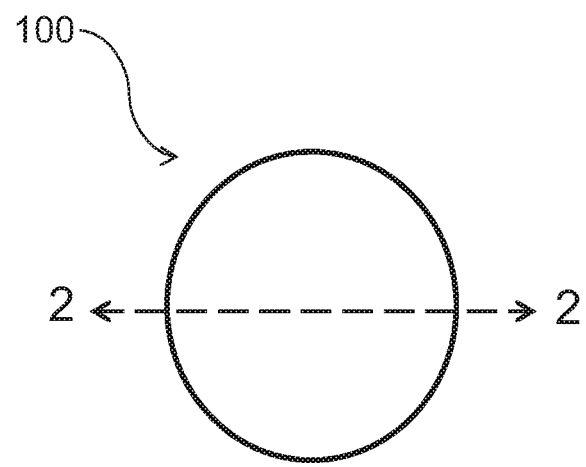
FIG. 1 is a top view of the pharmaceutical composition according to one embodiment of the present disclosure in the form of a tablet.

Repeat use of reference characters in the present specification and drawing is intended to represent the same or analogous features or elements of the present invention.

DETAILED DESCRIPTION OF REPRESENTATIVE EMBODIMENTS

It is to be understood by one of ordinary skill in the art that the present discussion is a description of exemplary embodiments only, and is not intended as limiting the broader aspects of the present invention.

Generally speaking, the present invention is directed to a solid pharmaceutical composition that can treat cystinuria. The solid pharmaceutical composition includes a core, an inner coating, and an outer coating. The core includes an active agent (e.g., tiopronin). Further, the inner coating, which includes a cellulose-based polymer, surrounds the core, and the outer coating, which includes an enteric polymer, surrounds the inner coating. As a result of the specific components of the solid pharmaceutical composition, as well as the weight percentages of the specific components of the solid pharmaceutical composition, the solid pharmaceutical composition is a delayed release composition and exhibits a fed state maximum plasma concentration ($C_{max}$) of tiopronin that is at least 70% of a fasted state maximum plasma concentration ($C_{max}$) of tiopronin after oral administration of the solid pharmaceutical composition. As such, it is possible for the solid pharmaceutical composition of the present invention to be administered orally with food or without food while still achieving a desired maximum plasma concentration of the active agent (e.g., tiopronin). In stark contrast, the tiopronin pharmaceutical compositions that are currently prescribed require a dosing frequency of three times a day and the current package labeling states that the tiopronin pharmaceutical composition is to be taken at least one hour before or at least two hours after a meal. Meanwhile, since the solid pharmaceutical composition of the present invention exhibits the characteristics of a delayed release composition and can be taken with food and a patient would not have to take his or her prescribed dose at least one hour before are at least two hours after a meal, patient compliance can be improved.

Figure 2:
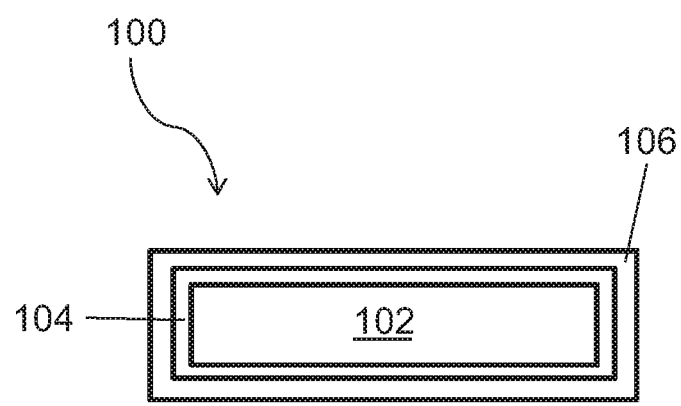
FIG. 2 is a cross-sectional side view of the tablet of FIG. 1 taken at line 2-2.

Referring to FIGS. 1 and 2, the solid pharmaceutical composition 100 of the present invention can be in the form of a tablet, pill, or capsule. Further, as shown in FIG. 2, which is a cross-sectional side view of the solid pharmaceutical composition 100 in the form of a tablet, the solid pharmaceutical composition 100 can include a core 102, an inner coating 104, and an outer coating 106. As shown, the inner coating 104 can completely surround the core 102, and the outer coating 106 can completely surround the inner coating 104.

I. Solid Pharmaceutical Composition a. Core

As described above, the solid pharmaceutical composition of the present invention includes a core. The core includes an active agent for the treatment of cystinuria. In addition, the core can include a diluent, a binder, a disintegrant, a lubricant, or a combination thereof. Each of the components of the core is discussed in more detail below.

i. Active Agent

In one particular embodiment, the solid pharmaceutical composition of the present invention includes an active agent suitable for the treatment of cystinuria. For instance, the active agent can be tiopronin, as represented by Structure I below:

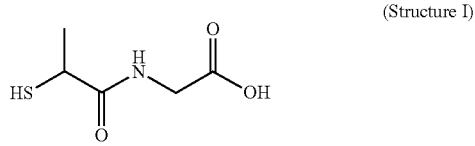

(Structure I)

The chemical formula for tiopronin is $C_5H_9NO_3S$, and it is also referred to as 2-(2-sulfanylpropanoylamino)acetic acid or 2-mercaptopropionylglycine, and is the active agent in THIOLA®, a tablet administered orally and indicated for the prevention of cystine kidney stones.

The amount of active agent (e.g., tiopronin) contained in the solid pharmaceutical composition of the present invention, including the core, inner coating, and outer coating, can range from about 35 wt. % to about 75 wt. %, such as from 40 wt. % to about 70 wt. %, such as from about 45 wt. % to about 65 wt. % based on the total weight of the solid pharmaceutical composition.

Further, the total weight of the active agent (e.g., tiopronin) in the solid pharmaceutical composition can range from about 50 milligrams to about 1000 milligrams, such as from about 75 milligrams to about 500 milligrams, such as from about 100 milligrams to about 300 milligrams. For instance, the solid pharmaceutical composition of the present invention can be in the form of a tablet, pill, or capsule that includes 100 milligrams of the active agent, 200 milligrams of the active agent, 300 milligrams of the active agent, etc.

ii. Diluent

In addition to an active agent, the core of the solid pharmaceutical composition can also include a diluent. The diluent can improve the uniformity of the solid pharmaceutical composition. Although any suitable diluent can be utilized, in some embodiments, the diluent can include a starch, a sugar alcohol, lactose, cellulose, microcrystalline cellulose, calcium phosphate, or a combination thereof. Suitable starches can include hydrolyzed starches or partially pregelatinized starches. Suitable sugar alcohols can include sorbitol, mannitol, or xylitol. Suitable lactoses can include anhydrous lactose or lactose monohydrate. In one particular embodiment, the diluent can be lactose monohydrate. In particular, it is believed that when lactose monohydrate is used as diluent, the stability of the solid pharmaceutical composition may be improved compared to using a starch or anhydrous lactose as the diluent.

Regardless of the particular diluent or combination of diluents utilized, the amount of diluent contained in the solid pharmaceutical composition of the present invention, including the core, inner coating, and outer coating, can range from about 10 wt. % to about 50 wt. %, such as from 15 wt. % to about 45 wt. %, such as from about 20 wt. % to about 40 wt. % based on the total weight of the solid pharmaceutical composition.

iii. Binder

Further, in some embodiments, the core of the solid pharmaceutical composition can also include a binder to aid in the granulation process, where the various components of the composition can be accumulated to former larger particles or granules.

In one embodiment, the binder can include a cellulose derivative (e.g., cellulosic ethers or esters). In one particular embodiment, for instance, the cellulose derivative can be a nonionic, cationic, anionic, and/or amphoteric cellulosic ether. Nonionic cellulose ethers, for instance, may be produced in any manner known to those skilled in the art, such as by reacting alkali cellulose with ethylene oxide and/or propylene oxide, followed by reaction with methyl chloride, ethyl chloride and/or propyl chloride. Some suitable examples of nonionic cellulosic ethers include, but are not limited to, water-soluble alkyl cellulose ethers, such as methyl cellulose and ethyl cellulose; hydroxyalkyl cellulose ethers, such as hydroxyethyl cellulose, hydroxypropyl cellulose, hydroxypropyl hydroxybutyl cellulose, hydroxyethyl hydroxypropyl cellulose, hydroxyethyl hydroxybutyl cellulose and hydroxyethyl hydroxypropyl hydroxybutyl cellulose; alkyl hydroxyalkyl cellulose ethers, such as methyl hydroxyethyl cellulose, hydroxypropyl methylcellulose, ethyl hydroxyethyl cellulose, ethyl hydroxypropyl cellulose, methyl ethyl hydroxyethyl cellulose and methyl ethyl hydroxypropyl cellulose; and so forth. Preferred nonionic cellulosic ethers for use in the composition of the present invention are ethyl hydroxyethyl cellulose, methylethyl hydroxyethyl cellulose, methylethyl hydroxyethyl hydroxypropyl cellulose, and hydroxypropyl methylcellulose. In one particular embodiment, the binder can include hydroxypropyl cellulose.

The amount of binder contained in the solid pharmaceutical composition of the present invention, including the core, inner coating, and outer coating, can range from about 0.25 wt. % to about 3 wt. %, such as from 0.5 wt. % to about 2.5 wt. %, such as from about 0.75 wt. % to about 2 wt. % based on the total weight of the solid pharmaceutical composition.

iv. Disintegrant

In addition, the core of the solid pharmaceutical composition can also include a disintegrant. A disintegrant is often used in the formation of a solid pharmaceutical composition because it may be difficult for many components contained in the solid pharmaceutical composition to be adequately disintegrated to such an extent as to exhibit a sufficient drug effect. Likewise, when such components are formed into tablets or granules, they may fail to retain their form owing to poor binding properties. In such cases, disintegration properties or binding properties can be imparted by adding a disintegrant to the composition.

Although any suitable disintegrant can be used, in some embodiments, the disintegrant can include a starch, a starch derivative, cellulose, a cellulose derivative, a clay, or a combination thereof. In one particular embodiment, the disintegrant can include low-substituted hydroxypropyl cellulose. Besides low-substituted hydroxypropyl cellulose, additives used for this purpose can include carboxymethylcellulose calcium, crosslinked carboxymethylcellulose sodium, crosslinked polyvinyl pyrrolidone, carboxymethyl starch, or a combination thereof. However, low-substituted hydroxypropyl cellulose may be particularly suitable in that it is nonionic and is therefore less susceptible to changes in properties due to reaction with, for instance, ionic drugs.

Regardless of the particular disintegrant utilized, the amount of disintegrant contained in the solid pharmaceutical composition of the present invention, including the core, inner coating, and outer coating, can range from about 1 wt. % to about 10 wt. %, such as from 1.5 wt. % to about 8 wt.

%, such as from about 2 wt. % to about 6 wt. % based on the total weight of the solid pharmaceutical composition.

v. Lubricant

Moreover, in some embodiments, the core of the solid pharmaceutical composition can include a lubricant. For instance, the core can include a stearate, stearic acid, hydrogenated vegetable oil, polyethylene glycol, or a combination thereof as a lubricant. Suitable stearates include magnesium stearate, zinc stearate, calcium stearate, or a combination of the above. In one particular embodiment, the lubricant comprises magnesium stearate.

Regardless of the particular lubricant utilized, the amount of lubricant contained in the solid pharmaceutical composition of the present invention, including the core, inner coating, and outer coating, can range from about 0.25 wt. % to about 3 wt. %, such as from 0.5 wt. % to about 2.5 wt. %, such as from about 0.75 wt. % to about 2 wt. % based on the total weight of the solid pharmaceutical composition.

b. Inner Coating

As described above, the core can be surrounded by an inner coating. The inner coating can include a coating polymer, where the inner coating can help prevent the coating polymer in the outer coating, which is discussed in more detail below, from interfering with the active agent, while also not affecting the desired release profile of the active agent (e.g., tiopronin).

The coating polymer contained in the inner coating can be water soluble. In one particular embodiment, the coating polymer contained in the inner coating can be a cellulose derivative (e.g., cellulosic ethers or esters). In one particular embodiment, for instance, the cellulose derivative can be a nonionic, cationic, anionic, and/or amphoteric cellulosic ether. Nonionic cellulose ethers, for instance, may be produced in any manner known to those skilled in the art, such as by reacting alkali cellulose with ethylene oxide and/or propylene oxide, followed by reaction with methyl chloride, ethyl chloride and/or propyl chloride. Some suitable examples of nonionic cellulosic ethers include, but are not limited to, water-soluble alkyl cellulose ethers, such as methyl cellulose and ethyl cellulose; hydroxyalkyl cellulose ethers, such as hydroxyethyl cellulose, hydroxypropyl cellulose, hydroxypropyl hydroxybutyl cellulose, hydroxyethyl hydroxypropyl cellulose, hydroxyethyl hydroxybutyl cellulose and hydroxyethyl hydroxypropyl hydroxybutyl cellulose; alkyl hydroxyalkyl cellulose ethers, such as methyl hydroxyethyl cellulose, hydroxypropyl methylcellulose, ethyl hydroxyethyl cellulose, ethyl hydroxypropyl cellulose, methyl ethyl hydroxyethyl cellulose and methyl ethyl hydroxypropyl cellulose; and so forth. Preferred nonionic cellulosic ethers for use in the composition of the present invention are ethyl hydroxyethyl cellulose, methylethyl hydroxyethyl cellulose, methylethyl hydroxyethyl hydroxypropyl cellulose, and hydroxypropyl methylcellulose.

Particularly suitable cellulosic ethers may include, for instance, those available from Dow Chemical under the name METHOCEL™ and having a methoxyl content of from about 15% to about 40%, such as from about 20% to about 35%, such as from about 25% to about 30%, a hydroxypropyl content of from about 1% to about 20%, such as from about 2.5% to about 17.5%, such as from about 5% to about 15%. Such hydroxypropyl methylcellulose cellulose derivatives can have a viscosity determined 2% in an aqueous solution at 20° C. ranging from about 1 mPa·s to about 10 mPa·s, such as from about 2 mPa·s to about 8 mPa·s, such as from 4 mPa·s to about 6 mPa·s. One suitable cellulosic ether is METHOCEL™ E5, a hydroxypropyl methylcellulose having a methoxyl content of 28% to 30%, a hydroxypropyl content of 7% to 12%, and a viscosity of 4 mPa·s to 6 mPa·s. Another particularly suitable cellulosic ether is SPECTRACEL™ 5 FG, which is also a hydroxypropyl methylcellulose having a methoxyl content of 28% to 30%, a hydroxypropyl content of 7% to 12%, and a viscosity of 4 mPa·s to 6 mPa·s. The present inventor has found when such hydroxypropyl methylcelluloses are used in forming the inner coating of the present invention, the inner coating can be easily sprayed to coat the core. Without intending to be limited by any particular theory, it is believed that the low viscosity of the hydroxypropyl methylcellulose in solution allows it to be sprayable during the process of forming the coating around the core, and it also exhibits excellent film-forming properties. In addition, the solubility of the hydroxypropyl methylcellulose results in negligible effects on the final tablet dissolution.

The amount of coating polymer contained in the solid pharmaceutical composition of the present invention, including the core, inner coating, and outer coating, can range from about 0.5 wt. % to about 10 wt. %, such as from 0.75 wt. % to about 7.5 wt. %, such as from about 1 wt. % to about 5 wt. % based on the total weight of the solid pharmaceutical composition.

c. Outer Coating

In addition to an inner coating, the solid pharmaceutical composition of the present invention can also include an outer coating, which can serve as an enteric coating to prevent the disintegration of the solid pharmaceutical composition in the gastric environment. The various components of the outer coating are discussed in more detail below.

i. Coating Polymer

First, the outer coating includes a coating polymer that prevents the disintegration or dissolution of the solid pharmaceutical composition in the gastric environment. As such, the coating polymer can be referred to as an enteric polymer. For instance, the enteric polymer can be composed of poly(methacrylic acid-co-methyl methacrylate), shellac (esters of aleurtic acid), cellulose acetate phthalate (CAP), cellulose acetate trimellitate (CAT), poly(vinyl acetate phthalate) (PVAP), hydroxypropyl methylcellulose phthalate (HPMCP), hydroxypropyl methylcellulose acetate succinate (HPMCAS), or a combination thereof.

Although any suitable enteric polymer can be used, in one embodiment, the outer coating can include an acrylic-based polymer. In one particular embodiment, the enteric polymer can include a methacrylic acid and ethyl acrylate copolymer. Further, the copolymer can be cationic or anionic. The enteric polymer can include the methacrylic acid and the ethyl acrylate in a ratio of from about 40:60 to about 65:35, such as from about 45:55 to about 60:40, such as about 50:50 (or 1:1). In one particular embodiment, the methacrylic acid and ethyl acrylate copolymer can be anionic. Further, the enteric polymer can have a molecular weight ranging from about 200,000 grams/mole to about 600,000 grams/mole, such as from about 250,000 grams/mole to about 500,000 grams/mole, such as from about 300,000 grams/mole to about 400,000 grams/mole. One particularly suitable copolymer is available under the name EUDRAGIT™ L 100-55, which includes methacrylic acid and ethyl acrylate in a 1:1 ratio, has a molecular weight of 320,000 grams/mole, and is soluble above pH of about 5.5.

Further, the enteric polymer can have a dissolution pH ranging from about 4.5 to about 6.5, such as from about 4.75 to about 6.25, such as from about 5 to about 6, where such a dissolution range mimics the pH conditions found in the proximal small intestine in the gastrointestinal tract.

The enteric polymer contained in the solid pharmaceutical composition of the present invention, including the core, inner coating, and outer coating, can range from about 0.25 wt. % to about 6 wt. %, such as from 0.5 wt. % to about 5 wt. %, such as from about 0.75 wt. % to about 4.5 wt. % based on the total weight of the solid pharmaceutical composition.

ii. Anti-Tacking Agent

In some embodiments, the outer coating may include an anti-tacking agent, which can be used to prevent sticking or clumping of the various components of the solid pharmaceutical composition during the coating application process. Suitable anti-tacking agents can include talc, cornstarch, synthetic amorphous silicon dioxide, DL-leucine, sodium lauryl sulfate, one or more metallic stearates, or a combination thereof. In one particular embodiment, the anti-tacking agent can include talc.

The anti-tacking agent contained in the solid pharmaceutical composition of the present invention, including the core, inner coating, and outer coating, can range from about 0.1 wt. % to about 4 wt. %, such as from 0.25 wt. % to about 3 wt. %, such as from about 0.5 wt. % to about 2 wt. % based on the total weight of the solid pharmaceutical composition.

iii. Plasticizer

The outer coating can also include a plasticizer. Suitable plasticizers can impart sufficient tensile strength to the outer coating to prevent film cracking. Such plasticizers can include triethyl citrate, dibutyl phthalate, polyethylene glycols, propylene glycol, diethylphthalate, acetyl triethyl citrate, or a combination thereof. In one particular embodiment, the plasticizer can be triethyl citrate.

The plasticizer contained in the solid pharmaceutical composition of the present invention, including the core, inner coating, and outer coating, can range from about 0.025 wt. % to about 1 wt. %, such as from 0.05 wt. % to about 0.75 wt. %, such as from about 0.075 wt. % to about 0.5 wt. % based on the total weight of the solid pharmaceutical composition.

II. Formation of the Solid Pharmaceutical Composition

Generally, the solid pharmaceutical composition of the present invention can be made by forming the core from the components discussed above and then coating the core with the inner coating. Thereafter, the outer coating is applied.

More specifically, the active ingredient (e.g., tiopronin) and the diluent (e.g., lactose (monohydrate)) can be granulated using an aqueous solution of a granulation aid (e.g., hydroxypropyl cellulose) via top-spray wet granulation in a fluid bed. Then, the resulting blend can be dried via the same fluid bed, after which the disintegrant (e.g., low-substituted hydroxypropyl cellulose) and lubricant (e.g., magnesium stearate) can be added, and a V-blender can then be used to form the core blend. The core blend can then be compressed into tablets via a rotary tablet press. The tablets can then be coated with the inner coating (e.g., hydroxypropyl methylcellulose) via a fully perforated coating pan. Next, the tablets can be coated with the outer coating (e.g., a blend of an enteric polymer such as Eudragit® L 100-55, an anti-tacking agent such as talc, and a plasticizer such as triethyl citrate) via a fully perforated coating pan.

Based on the specific components in the solid pharmaceutical composition, the present inventor has found that the solid pharmaceutical composition exhibits excellent stability. For instance, the amount of tiopronin present in the solid pharmaceutical composition after storage at 25° C. and a relative humidity of 60% for 9 months is at least 90%, such as at least 92%, such as at least 95%, of the amount of tiopronin present in the solid pharmaceutical composition prior to storage. Further, the amount of tiopronin present in the solid pharmaceutical composition after storage at 40° C. and a relative humidity of 75% for 6 months is at least 90%, such as at least 92%, such as at least 94%, of the amount of tiopronin present in the solid pharmaceutical composition prior to storage.

In addition, the solid pharmaceutical composition of the present invention can exhibit less than 10% dissolution, such as less than 8% dissolution, such as less than 6% dissolution, when exposed to a 0.1 N HCl solution for 120 minutes and greater than 70%, such as greater than 75%, such as greater than 80% dissolution when exposed to a phosphate buffer solution having a pH of 6.8 for 45 minutes. In contrast, the existing immediate release tiopronin formulation exhibits rapid dissolution in 0.1 N HCl, where the immediate release formulation exhibits greater than 90% dissolution after only 45 minutes. This distinction indicates that the solid pharmaceutical composition (e.g., solid tiopronin composition) of the present invention exhibits characteristics of a delayed release formulation in that it does not dissolve quickly in an acidic environment, such as the stomach.

III. Administration of the Solid Pharmaceutical Composition

The solid pharmaceutical composition of the present invention can be administered orally in a tablet, pill, or capsule form. Surprisingly, the present inventor has found that the composition of the present invention can be administered orally in a fed state (with food) and can exhibit a pharmacokinetic profile similar to when the composition of the present invention is administered in a 12-hour fasted state. For instance, the pharmacokinetic parameters of $C_{max}$, $T_{max}$, $AUC_{0-\infty}$, and $AUC_{0-t}$ achieved for the solid pharmaceutical composition of the present invention are discussed in more detail below.

As an initial matter, it is understood that $C_{max}$ refers to the maximum (or peak) plasma or serum concentration that a drug achieves in a specified compartment or test area of the body after the drug has been administrated and before the administration of a second dose. Further, $T_{max}$ refers to the time at which the $C_{max}$ is observed. In addition, the $AUC_{0-t}$ value refers to the area under the concentration-time curve up to the last measurable concentration (sometimes referred to as $AUC_{0-last}$), where the AUC is approximated by a series of trapezoids in which the area of all trapezoids is computed, and the areas are summed to give the AUC up to the last sample drawn. Meanwhile, the $AUC_{0-\infty}$ value refers to the total drug exposure over time to infinity based on a calculation of the total area under the concentration-time curve. Assuming linear pharmacokinetics with similar absorption and elimination rates, one can show that the AUC is proportional to the total amount of drug absorbed by the body. Because the assays used to calculate this value cannot go to infinity, infinity is extrapolated. For instance, this value can be calculated from the $AUC_{(0-t)}$ by the addition of a constant $(C_{last}/\lambda_z)$, where $C_{last}$ is the last observed quantifiable concentration and $\lambda_z$ is the terminal phase rate constant.

As mentioned above, surprisingly, the pharmacokinetic values of the solid pharmaceutical composition of the present invention are similar whether the composition is administered in a fed state or a 12-hour fasted state. For instance, when the solid pharmaceutical composition is administered orally in a 300 milligram dose, the fed state $C_{max}$ of tiopronin can be at least 70%, such as at least 75%, such as at least 80%, of the 12-hour fasted state $C_{max}$ of tiopronin. For example, the $C_{max}$ of tiopronin in the fed state can range from about 75% to about 99%, such as from about 80% to about 97.5%, such as from about 85% to about 95% of the $C_{max}$ of tiopronin in the 12-hour fasted stated. Likewise, the $C_{max}$ of tiopronin in the fed state can range from about 2000 nanograms/milliliter (ng/mL) to about 10,500 ng/mL, such as from about 2500 ng/mL to about 10,000 ng/mL, such as from about 3000 ng/mL to about 9500 ng/mL when tiopronin is used as the active agent in the solid pharmaceutical composition of the present invention. Meanwhile, the $C_{max}$ of tiopronin in the 12-hour fasted state can range from about 1500 ng/mL to about 11,000 ng/mL, such as from about 3000 ng/mL to about 10,500 ng/mL, such as from about 4000 ng/mL to about 10,000 ng/m L when tiopronin is used as the active agent in the solid pharmaceutical composition of the present invention.

Further, the fed state $T_{max}$ can be from about 100% to about 140%, such as from about 105% to about 135%, such as from about 110% to about 130% of the 12-hour fasted state $T_{max}$ when tiopronin is the active agent in the solid pharmaceutical composition of the present invention and when the solid pharmaceutical composition is administered orally in a 300 milligram dose. For example, the fed state $T_{max}$ can range from about 2.5 hours to about 6.5 hours, such as from about 2.75 hours to about 6.25 hours, such as from about 3 hours to about 6 hours. On the other hand, the 12-hour fasted state $T_{max}$ can range from about 1 hour to about 6 hours, such as from about 1.25 hours to about 5 hours, such as from about 1.5 hours to about 4 hours.

In addition, when tiopronin is the active agent in the solid pharmaceutical composition of the present invention and when the solid pharmaceutical composition is administered orally in a 300 milligram dose, the fed state $AUC_{0-\infty}$ of tiopronin can be at least 60%, such as at least 65%, such as at least 70% of the 12-hour fasted state $AUC_{0-\infty}$ of tiopronin. For instance, the fed state $AUC_{0-\infty}$ of tiopronin can be from about 65% to about 99%, such as from about 90% to about 95%, such as from about 75% to about 90% of the 12-hour fasted state $AUC_{0-\infty}$ of tiopronin. Moreover, the fed state $AUC_{0-\infty}$ of tiopronin can range from about 16,000 hours*ng/mL to about 48,000 hours*ng/mL, such as from about 18,000 hours*ng/mL to about 46,000 hours*ng/mL, such as from about 20,000 hours*ng/mL to about 44,000 hours*ng/mL, while the 12-hour fasted state $AUC_{0-\infty}$ of tiopronin can range from about 16,000 hours*ng/mL to about 70,000 hours*ng/mL, such as from about 20,000 hours*ng/mL to about 65,000 hours*ng/mL, such as from about 24,000 hours*ng/mL to about 60,000 hours*ng/m L.

Further, when tiopronin is the active agent in the solid pharmaceutical composition of the present invention and when the solid pharmaceutical composition is administered orally in a 300 milligram dose, the fed state $AUC_{0-t}$ of tiopronin can be at least 60%, such as at least 65%, such as at least 70% of the fasted state $AUC_{0-t}$ of tiopronin. For instance, the fed state $AUC_{0-t}$ of tiopronin can be from about 65% to about 99%, such as from about 70% to about 95%, such as from about 75% to about 90% of the 12-hour fasted state $AUC_{0-t}$ of tiopronin. Moreover, the fed state $AUC_{0-t}$ of tiopronin can range from about 12,000 hours*ng/mL to about 40,000 hours*ng/mL, such as from about 14,000 hours*ng/mL to about 38,000 hours*ng/mL, such as from about 16,000 hours*ng/mL to about 36,000 hours*ng/mL, while the 12-hour fasted state $AUC_{0-t}$ of tiopronin can range from about 8000 hours*ng/mL to about 54,000 hours*ng/mL, such as from about 16,000 hours*ng/mL to about 52,000 hours*ng/mL, such as from about 20,000 hours*ng/mL to about 50,000 hours*ng/mL.

In addition, when the solid pharmaceutical composition is administered orally in a 300 milligram dose, the mean fed state $C_{max}$ of tiopronin can range from about 4500 ng/mL to about 7000 ng/mL, such as from about 4750 ng/mL to about 6750 ng/mL, such as from about 5000 ng/mL to about 6000 ng/mL, and the median fed state $C_{max}$ of tiopronin range from about 4000 ng/mL to about 6500 ng/mL, such as from about 4500 ng/mL to about 6250 ng/mL, such as from about 4750 ng/mL to about 5750 ng/mL when tiopronin is used as the active agent in the solid pharmaceutical composition of the present invention. Further, when the solid pharmaceutical composition is administered orally in a 300 milligram dose, the mean 12-hour fasted state $C_{max}$ of tiopronin can range from about 5000 ng/mL to about 8000 ng/mL, such as from about 5500 ng/mL to about 7750 ng/mL, such as from about 5750 ng/mL to about 7000 ng/mL, and the median 12-hour fasted state $C_{max}$ of tiopronin range from about 5000 ng/mL to about 7750 ng/mL, such as from about 5250 ng/mL to about 7500 ng/mL, such as from about 5750 ng/mL to about 6750 ng/mL when tiopronin is used as the active agent in the solid pharmaceutical composition of the present invention.

Moreover, when the solid pharmaceutical composition is administered orally in a 300 milligram dose, the mean fed state $T_{max}$ can range from about 3 hours to about 4.75 hours, such as from about 3.25 hours to about 4.5 hours, such as from about 3.5 hours to about 4.25 hours, and the median fed state $T_{max}$ can range from about 2.75 hours to about 4.5 hours, such as from about 3 hours to about 4.25 hours, such as from about 3.25 hours to about 4 hours when tiopronin is used as the active agent in the solid pharmaceutical composition of the present invention. Further, when the solid pharmaceutical composition is administered orally in a 300 milligram dose, the mean 12-hour fasted state $T_{max}$ can range from about 2.5 hours to about 3.8 hours, such as from about 2.6 hours to about 3.7 hours, such as from about 2.7 hours to about 3.4 hours, and the median 12-hour fasted state $T_{max}$ can range from about 2.4 hours to about 3.75 hours, such as from about 2.5 hours to about 3.6 hours, such as from about 2.6 hours to about 3.3 hours when tiopronin is used as the active agent in the solid pharmaceutical composition of the present invention.

Furthermore, when the solid pharmaceutical composition is administered orally in a 300 milligram dose, the mean fed state $AUC_{0-\infty}$ can range from about 24,500 hours*ng/mL to about 38,500 hours*ng/mL, such as from about 26,000 hours*ng/mL to about 36,000 hours*ng/mL, such as from about 27,500 hours*ng/mL to about 33,500 hours*ng/mL, and the median fed state $AUC_{0-\infty}$ can range from about 22,500 hours*ng/mL to about 35,250 hours*ng/mL, such as from about 24,000 hours*ng/mL to about 33,750 hours*ng/mL, such as from about 25,500 hours*ng/mL to about 32,250 hours*ng/mL when tiopronin is used as the active agent in the solid pharmaceutical composition of the present invention. Meanwhile, when the solid pharmaceutical composition is administered orally in a 300 milligram dose, the mean 12-hour fasted state $AUC_{0-\infty}$ can range from about 31,000 hours*ng/mL to about 48,000 hours*ng/mL, such as from about 33,000 hours*ng/mL to about 46,000 hours*ng/mL, such as from about 35,000 hours*ng/mL to about 42,000 hours*ng/mL, and the median 12-hour fasted state $AUC_{0-\infty}$ can range from about 30,000 hours*ng/mL to about 47,000 hours*ng/mL, such as from about 32,000 hours*ng/mL to about 45,000 hours*ng/mL, such as from about 34,000 hours*ng/mL to about 41,000 hours*ng/mL when tiopronin is used as the active agent in the solid pharmaceutical composition of the present invention.

Likewise, when the solid pharmaceutical composition is administered orally in a 300 milligram dose, the mean fed state $AUC_{0-t}$ can range from about 20,000 hours*ng/mL to about 31,000 hours*ng/mL, such as from about 21,000 hours*ng/mL to about 29,000 hours*ng/mL, such as from about 22,000 hours*ng/mL to about 27,000 hours*ng/mL, and the median fed state $AUC_{0-t}$ can range from about 19,000 hours*ng/mL to about 30,000 hours*ng/mL, such as from about 20,000 hours*ng/mL to about 29,000 hours*ng/mL, such as from about 21,000 hours*ng/mL to about 27,000 hours*ng/mL when tiopronin is used as the active agent in the solid pharmaceutical composition of the present invention. Meanwhile, when the solid pharmaceutical composition is administered orally in a 300 milligram dose, the mean 12-hour fasted state $AUC_{0-t}$ can range from about 26,000 hours*ng/mL to about 40,000 hours*ng/mL, such as from about 28,000 hours*ng/mL to about 39,000 hours*ng/mL, such as from about 30,000 hours*ng/mL to about 36,000 hours*ng/mL, and the median 12-hour fasted state $AUC_{0-t}$ can range from about 25,000 hours*ng/mL to about 40,000 hours*ng/mL, such as from about 27,000 hours*ng/mL to about 38,000 hours*ng/mL, such as from about 29,000 hours*ng/mL to about 35,000 hours*ng/mL when tiopronin is used as the active agent in the solid pharmaceutical composition of the present invention. The present invention may be better understood by reference to the following examples.

EXAMPLE 1

A solid pharmaceutical composition was formed that included 100 milligrams of tiopronin. The weight percentages of the components used in the formation of 100 milligram (mg) tiopronin tablets are summarized below in Table 1.

TABLE 1

100 mg Tiopronin Tablet Components
100 mg Tiopronin Enteric Coated Tablet Formulation

| Ingredient | Function | Location | mg/Tablet | Wt. % |
|---|---|---|---|---|
| Tiopronin | Active Ingredient | Core | 100.00 | 53.79 |
| Lactose (Monohydrate) | Diluent | Core | 54.37 | 29.24 |
| Hydroxypropyl Cellulose | Granulation Aid/Binder | Core | 3.00 | 1.61 |
| Hydroxypropyl Cellulose (Low Substituted) | Disintegrant | Core | 10.33 | 5.56 |
| Magnesium Stearate | Lubricant | Core | 2.70 | 1.45 |
| Hydroxypropyl Methylcellulose E5 | Coating Polymer | Inner Coating | 5.11 | 2.75 |
| Eudragit ™ L 100-55 | Coating Polymer | Outer Coating | 6.51 | 3.50 |
| Talc | Anti-Tacking Agent | Outer Coating | 3.25 | 1.75 |
| Triethyl Citrate | Plasticizer | Outer Coating | 0.65 | 0.35 |

Then, a sample size of 300,000 tablets each containing 100 mg of tiopronin were then subjected to a long-term stability study where 300 tablets were stored in a high density polyethylene container with a polypropylene-based closure material and a charcoal/silica desiccant for a time period of 9 months at a temperature of 25° C. and a relative humidity of 60%. Tiopronin assays were performed at time 0, 1 month, 2 months, 3 months, 6 months, and 9 months. At time 0, the assay indicated the presence of 98.8% of the 100 mg of tiopronin. The percentage was 98.3% at 1 month, 100.3% at 2 months, 97.2% at 3 months, 98.3% at 6 months, and 95.4% at 9 months, indicating that the tiopronin level was generally maintained at 100 mg over the 9 month time frame, indicating a stable composition.

Next, an additional sample size of 300,000 tablets each containing 100 mg of tiopronin were then subjected to an accelerated stability study where 300 tablets were stored in a high density polyethylene container with a polypropylene-based closure material and a charcoal/silica desiccant for a time period of 6 months at a temperature of 40° C. and a relative humidity of 75%. Tiopronin assays were performed at time 0, 1 month, 2 months, 3 months, and 6 months. At time 0, the assay indicated the presence of 98.8% of the 100 mg of tiopronin. The percentage was 98.1% at 1 month, 98.5% at 2 months, 98.7% at 3 months, and 94.3% at 6 months, indicating that the tiopronin level was generally maintained at 100 mg over the 6 month time frame, which corresponds with an extremely stable composition.

EXAMPLE 2

A solid pharmaceutical composition was formed that included 300 milligrams of tiopronin. The weight percentages of the components used in the formation of 300 milligram (mg) tiopronin tablets are summarized below in Table 2.

TABLE 2

300 mg Tiopronin Tablet Components
300 mg Tiopronin Enteric Coated Tablet Formulation

| Ingredient | Function | Location | mg/Tablet | Wt. % |
|---|---|---|---|---|
| Tiopronin | Active Ingredient | Core | 300.00 | 55.88 |
| Lactose (Monohydrate) | Diluent | Core | 163.11 | 30.38 |
| Hydroxypropyl Cellulose | Granulation Aid/Binder | Core | 9.00 | 1.68 |
| Hydroxypropyl Cellulose (Low Substituted) | Disintegrant | Core | 30.99 | 5.77 |
| Magnesium Stearate | Lubricant | Core | 8.10 | 1.51 |
| Hydroxypropyl Methylcellulose E5 | Coating Polymer | Inner Coating | 15.34 | 2.86 |
| Eudragit ™ L 100-55 | Coating Polymer | Outer Coating | 6.43 | 1.20 |
| Talc | Anti-Tacking Agent | Outer Coating | 3.22 | 0.60 |
| Triethyl Citrate | Plasticizer | Outer Coating | 0.64 | 0.12 |

Then, a sample size of 100,000 tablets each containing 300 mg of tiopronin were then subjected to a long-term stability study where 90 tablets were stored in a high density polyethylene container with a polypropylene-based closure material and a charcoal/silica desiccant for a time period of 9 months at a temperature of 25° C. and a relative humidity of 60%. Tiopronin assays were performed at time 0, 1 month, 2 months, 3 months, and 9 months. At time 0, the assay indicated the presence of 97.4% of the 300 mg of tiopronin. The percentage was 100.2% at 1 month, 99.7% at 2 months, 100.1% at 3 months, 97.0% at 6 months, and 98.9% at 9 months, indicating that the tiopronin level was generally maintained at 300 mg over the 9 month time frame, which corresponds with an extremely stable composition.

Next, an additional sample size of 100,000 tablets each containing 300 mg of tiopronin were then subjected to an accelerated stability study where 90 tablets were stored in a high density polyethylene container with a polypropylene-based closure material and a charcoal/silica desiccant for a time period of 6 months at a temperature of 40° C. and a relative humidity of 75%. Tiopronin assays were performed at time 0, 1 month, 2 months, 3 months, and 6 months. At time 0, the assay indicated the presence of 97.4% of the 300 mg of tiopronin. The percentage was 96.7% at 1 month, 99.6% at 2 months, 98.0% at 3 months, and 94.7% at 6 months, indicating that the tiopronin level was generally maintained at 300 mg over the 6 month time frame, which corresponds with an extremely stable composition.

In addition, a pharmacokinetic study was performed on the 300 milligram enteric coated tiopronin tablets that were administered orally to 12 subjects in either a fed state or a 12-hour fasted state to evaluate the food effect on the bioavailability of the orally administered tiopronin enteric coated tablets of the present invention. In the study, a single 300 milligram dose of the tiopronin of the present invention was given orally in the 12-hour fasted state with a 72-hour pharmacokinetic profile assessment, and a single 300 milligram dose of the tiopronin of the present invention was given orally in the fed state with a 72-hour pharmacokinetic profile assessment.

The primary pharmacokinetic parameters to evaluate the effect of food are area under the concentration-time curve from 0 hours to infinity ($AUC_{0-\infty}$), area under the concentration-time curve from 0 hours to the last measurable concentration ($AUC_{0-t}$), and maximum concentration ($C_{max}$). The secondary pharmacokinetic parameters to evaluate the effect of food are time of the maximum concentration ($T_{max}$), half-life ($t_{1/2}$), and, if present, lag time ($T_{lag}$).

An LC-MS/MS method was developed and validated for the analysis of free total tiopronin in human plasma treated with $K_2EDTA$. The method utilized 100 μL aliquot of plasma that was extracted with methanol containing d3-tiopronin as the internal standard. Separation for the analyte is achieved using reversed-phase chromatography coupled electrospray mass spectrometry (ESI) in the negative ion mode. The lower limit of quantitation is 50 ng/mL and a linear response function was established for the range of concentrations 50 to 5,000 ng/mL (r >0.99) for total tiopronin in human plasma.

Table 3 summarizes additional $C_{max}$, $T_{max}$, $AUC_{0-\infty}$, $AUC_{0-t}$, and additional pharmacokinetic data, indicating that orally administering tiopronin in a fed state results in a pharmacokinetic profile that is similar to when the tiopronin is orally administered in a 12-hour fasted state. From Table 3, it is determined that the fed state (standardized breakfast/high fat diet) decreased the plasma exposure of the drug compared to the fasted state as measured by $C_{max}$ by about 13%, while $AUC_{0-last}$ and $AUC_{0-\infty}$ were lowered by about 25% and about 22%, respectively.

TABLE 3

Tiopronin Pharmacokinetics - Fed vs. Fasted, 300 mg EC Tablets

| Parameter (units) Statistics | Fed | Fasted |
|---|---|---|
| $AUC_{0-\infty}$ (hr · ng/mL) | | |
| n | 12 | 12 |
| Mean ± SD | 30566.48 ± 8569.23 | 38901.60 ± 8938.33 |
| Median | 28199.84 | 37733.87 |
| Range | 21643.0-43902.0 | 24715.5-58056.6 |
| Geo Mean | 29504.14 | 37988.60 |
| CV(%) | 28.03 | 22.98 |
| $AUC_{0-last}$ (hr · ng/mL) | | |
| n | 12 | 12 |
| Mean ± SD | 24751.64 ± 6213.23 | 32681.20 ± 7393.88 |
| Median | 23991.23 | 31638.92 |
| Range | 17218.5-35898.9 | 21194.0-48243.5 |
| Geo Mean | 24051.36 | 31939.30 |
| CV(%) | 25.10 | 22.62 |
| $C_{max}$ (ng/mL) | | |
| n | 12 | 12 |
| Mean ± SD | 5641.67 ± 1776.71 | 6408.33 ± 1674.01 |
| Median | 5255.00 | 6310.00 |
| Range | 3060.0-9300.0 | 4080.0-8950.0 |
| Geo Mean | 5396.80 | 6200.49 |
| CV(%) | 31.49 | 26.12 |
| $t_{1/2}$ (hr) | | |
| n | 12 | 12 |
| Mean ± SD | 46.26 ± 10.61 | 40.94 ± 3.87 |
| Median | 44.44 | 39.60 |
| Range | 35.1-66.3 | 33.5-46.2 |
| CV(%) | 22.93 | 9.46 |
| $T_{lag}$ (hr) | | |
| n | 12 | 12 |
| Mean ± SD | 1.76 ± 0.32 | 1.17 ± 0.39 |
| Median | 2.00 | 1.28 |
| Range | 1.1-2.0 | 0.5-1.5 |
| CV(%) | 18.41 | 33.10 |
| $T_{max}$ | | |
| n | 12 | 12 |
| Mean ± SD | 3.84 ± 1.11 | 3.05 ± 0.86 |
| Median | 3.55 | 3.00 |
| Range | 3.0-6.0 | 1.5-4.0 |
| CV(%) | 28.84 | 28.20 |

Under the fasted state, the mean absorption $T_{lag}$ of tiopronin 300 mg EC was 1.17 hours, which is consistent with the stomach transit time of 0.5 to 1.0 hours in the fasted state. The standardized breakfast (high fat diet) delayed tiopronin absorption with a mean absorption $T_{lag}$ of 1.76 hours which might be caused by increased gastric emptying time. The observed fed state extended $T_{lag}$ assures tiopronin EC absorption is initiated in the proximal intestine similar to the fasted state. The $T_{max}$ was also slightly extended in the fed state with a mean 3.55 hours compared to 3.00 hours in the fasted state consistent with a delay in tiopronin absorption. The $t_{1/2}$ was very similar in both fasted and fed subjects with a mean 42.09 and 46.35 hours, respectively, suggesting no impact on the systemic elimination of tiopronin in the fed state.

Figure 3:
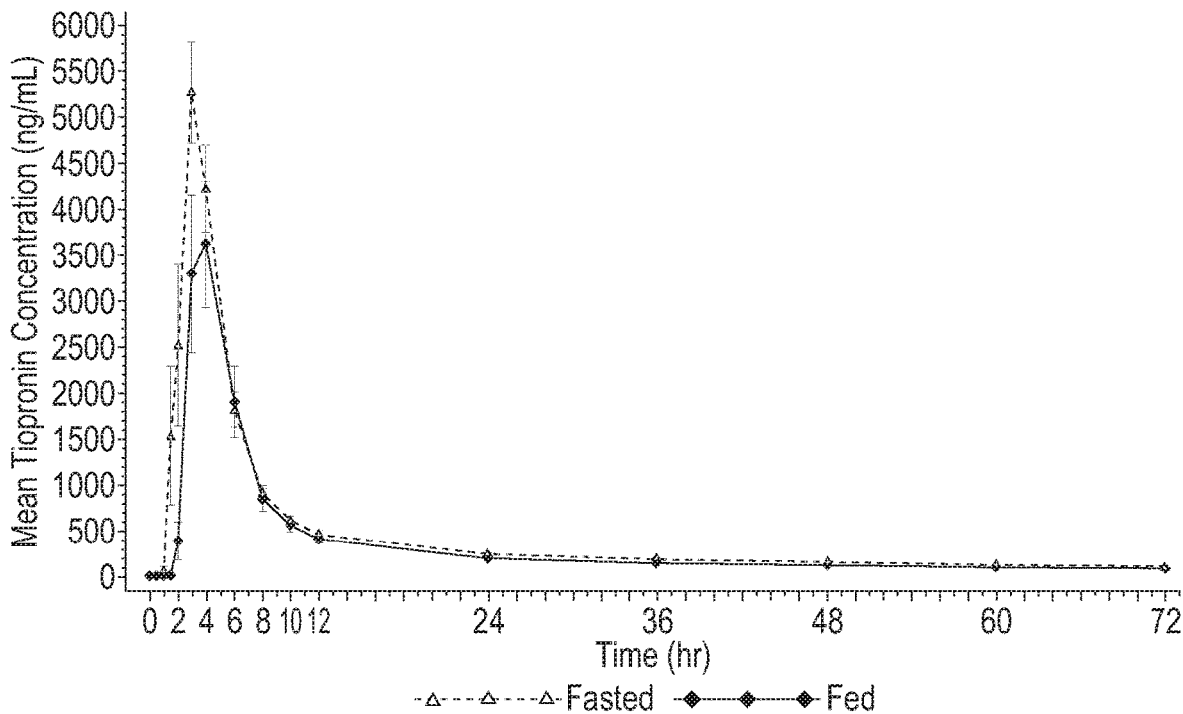
FIG. 3 is a graph illustrating the mean tiopronin concentration in plasma when the pharmaceutical composition is delivered in fasted state vs. a fed state over a 72-hour time period.
Figure 4:
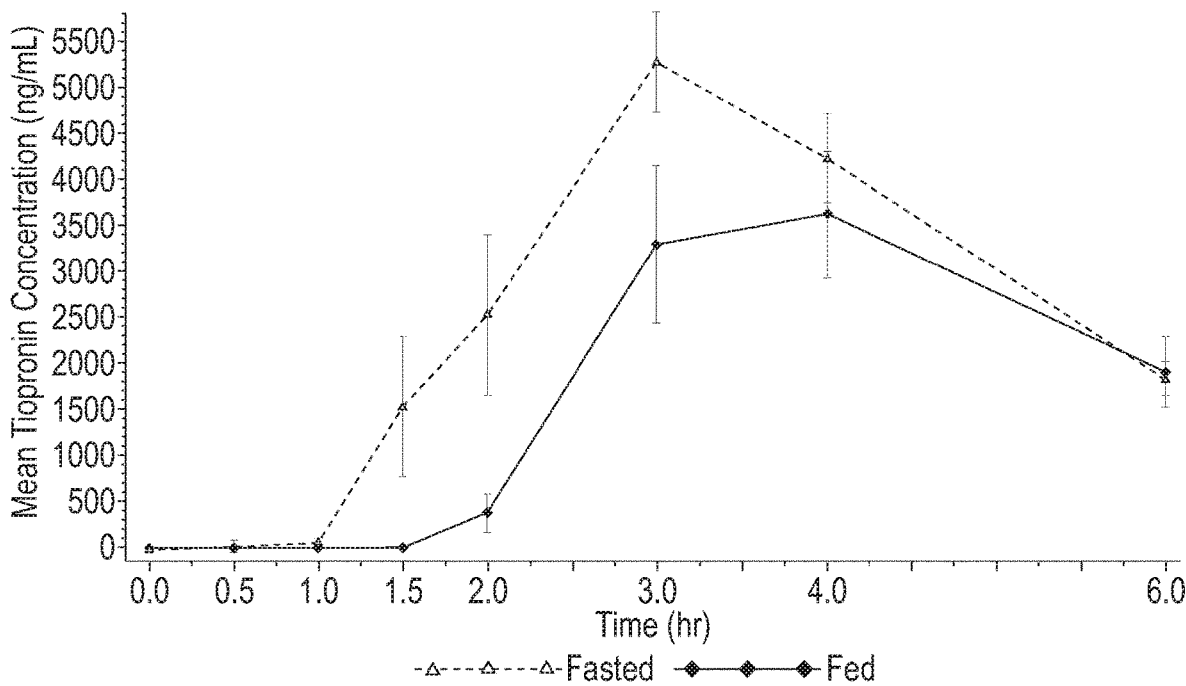
FIG. 4 is a zoomed-in view of the graph of FIG. 3 illustrating the mean tiopronin concentration in plasma when the pharmaceutical composition is delivered in a fasted state vs. a fed state over a 6-hour time period.

Further, the mean tiopronin concentration was determined over a 72 hour time period, and the results are shown in FIGS. 3 and 4. FIG. 3 is a graph comparing the tiopronin concentration over time, up to 72 hours, and shows that the distribution and elimination of tiopronin do not change after the standardized breakfast (high fat diet) compared to the 12-hour fasted stated. FIG. 4 is a zoomed in view of FIG. 3, showing the concentration of tiopronin over the first 6 hours after dosing. The observed tiopronin EC rapid absorption after 1 hour following dose administration under fasted condition indicates gastric by-pass of the EC solid dosage form, while the delayed absorption at 1.5 to 2.0 hours under fed conditions is very likely to be due to delayed gastric emptying.

Overall, the study findings indicate a food effect as expected with an absorption delay of approximately 0.6 hours for total tiopronin due to increased gastric emptying time in the high fat fed diet. In addition, there was a decrease in the bioavailability of total tiopronin in the fed state with tiopronin EC compared to the fasted state. The observed absorption delay of tiopronin EC under fed conditions should not alter disposition kinetics of the drug as the drug is expected to be absorbed throughout the gastrointestinal tract after by-passing the stomach. Also, there were no differences in the systemic elimination ($t_{1/2}$) of tiopronin between fasted and fed states indicating no impact on the drug elimination kinetics in the fed state. Therefore, the observed food effect for enteric coated tiopronin tablets of the present invention may not be clinically important, given that the drug is dosed to effect, and can be dosed in the fed or fasted state provided the drug is administered the same way every time.

EXAMPLE 3

A solid pharmaceutical composition was formed that included 300 milligrams of tiopronin. The weight percentages of the components used in the formation of 300 milligram (mg) enteric coated tiopronin tablets are summarized above in Table 2, Example 2.

Then, a pharmacokinetic study was performed evaluate the relative bioavailability of orally administered enteric-coated tiopronin 300 milligram tablets as formed according to Example 2 with 3 THIOLA® immediate release 100 milligram tablets, where both formulations were administered in a 12-hour fasted state.

The primary pharmacokinetic parameters are area under the curve ($AUC_{0-t}$ and $AUC_{0-\infty}$) and maximum concentration ($C_{max}$). The secondary pharmacokinetic parameters are time of the maximum concentration ($T_{max}$), elimination rate constant (Kel), and half-life ($t_{1/2}$).

Subjects received a standardized lunch 4 hours after ingestion of the study drug (following collection of the 4-hour blood sample and prior to the 6-hour blood sampling). The standardized meal was based on a 2,100-calorie diet for female subjects and a 2,600-calorie diet for male subjects (U.S. Department of Health and Human Services and U.S. Department of Agriculture. 2015-2020 Dietary Guidelines for Americans, 8th Edition, dated December 2015, available from health.gov). The dinner was also standardized on the dosing day. Subsequent meals and snacks were not standardized. Water consumption was allowed as desired except for 1 hour before and 1 hour after study drug administration.

A liquid chromatography with tandem mass spectrometry (LC-MS/MS) method was developed and validated for the analysis of total tiopronin in human plasma treated with $K_2EDTA$. The method utilized a 100-µL aliquot of plasma that was extracted with methanol containing d3-tiopronin as the internal standard. Separation for the analyte is achieved using reversed-phase chromatography coupled electrospray mass spectrometry (ESI) in the negative ion mode. The lower limit of quantitation (LLOQ) is 50 ng/mL and a linear response function was established for the range of concentrations 50 to 5,000 ng/mL (r >0.99) for total tiopronin in human plasma.

Figure 5:
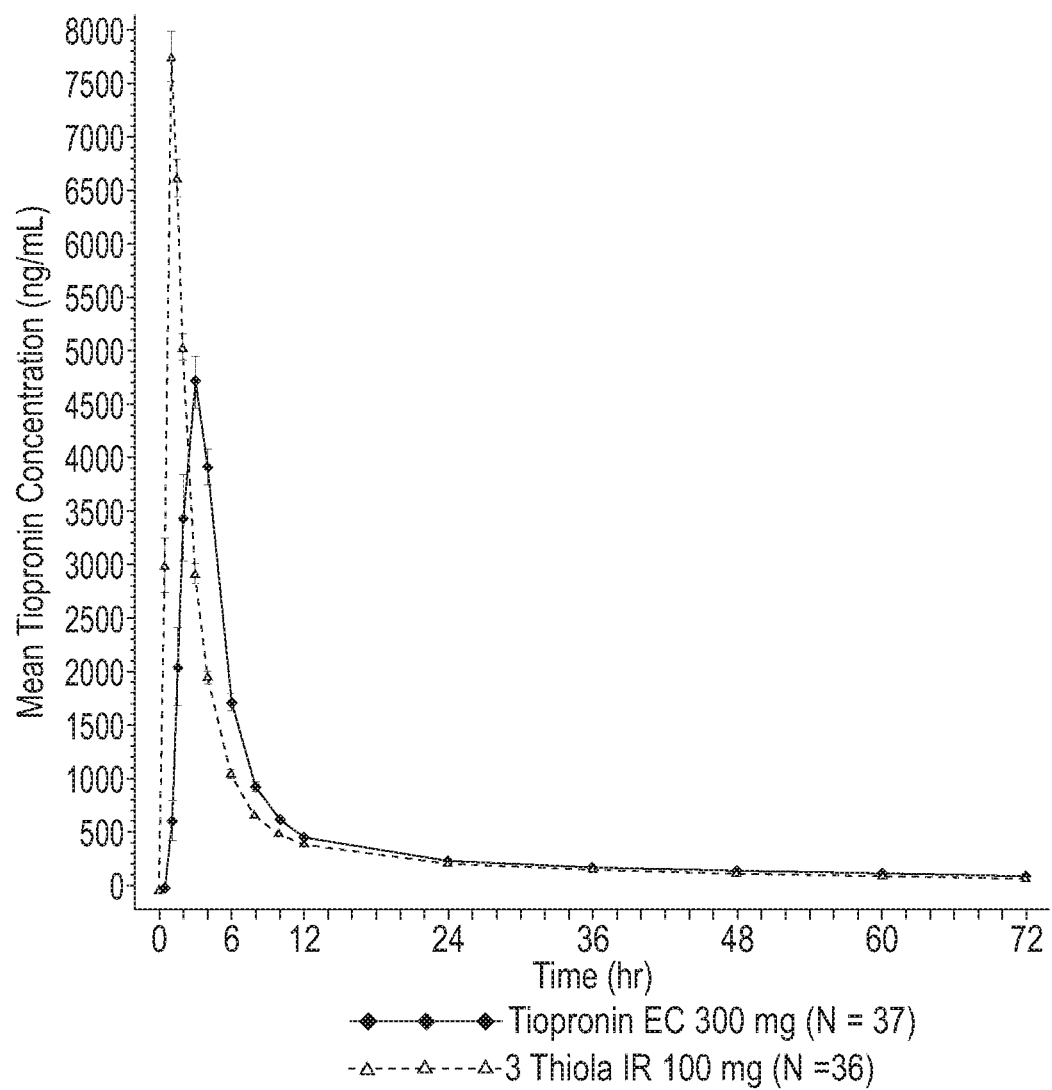
FIG. 5 a graph illustrating the mean tiopronin concentration in plasma when the pharmaceutical composition of the present invention is delivered in fasted state vs. when the immediate release formulation of tiopronin is delivered in a fasted state over a 72-hour time period.
Figure 6:
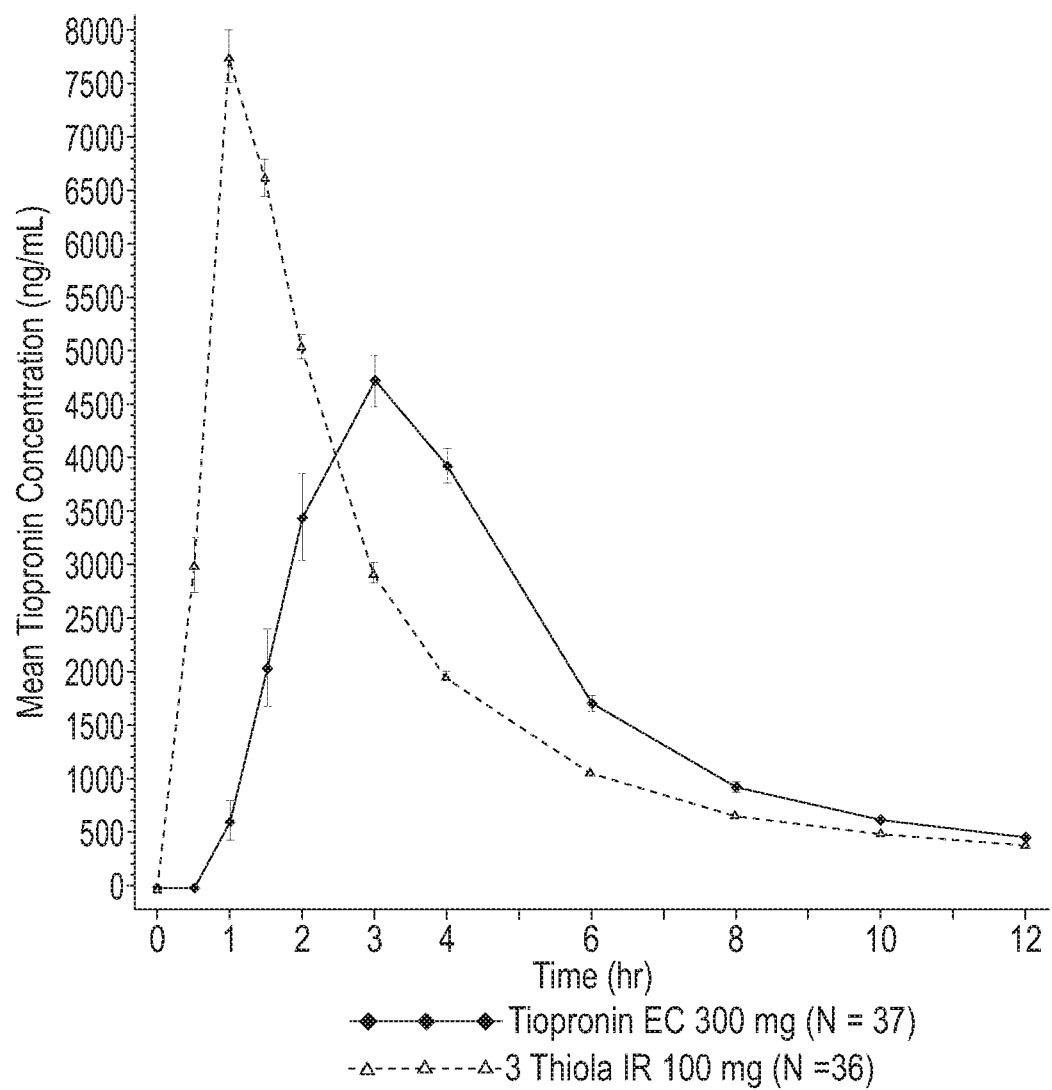
FIG. 6 is a zoomed-in view of the graph of FIG. 5 illustrating the mean tiopronin concentration in plasma when the pharmaceutical composition of the present invention is delivered in a fasted state vs. when the immediate release formulation of tiopronin is delivered in a fasted state over a 12-hour time period.

The mean (SE) tiopronin concentration over time for the enteric coated tiopronin 300 mg tablets of Example 2 and 3 THIOLA® immediate release (IR) tablets are illustrated in FIG. 5. FIG. 5 shows similar distribution and elimination phases for tiopronin in subjects treated with the enteric coated tiopronin 300 mg tablets of Example 2 and 3 THIOLA® immediate release (IR) tablets. The mean (SE) total tiopronin concentration over 0 to 12 hours is illustrated in FIG. 6.

As shown, the absorption of tiopronin after treatment with the enteric coated tiopronin 300 mg tablets of Example 2 begins approximately 0.5 to 1 hour after that observed for the 3 THIOLA® IR 100 mg tablets. This is an indication of modified release of the tiopronin EC 300 milligram formulation contemplated by the present invention, which is consistent with the stomach transit time of 0.5 hours to 1.0 hour in the fasted state. Also, the observed slower absorption rate of the tiopronin EC 300 milligram formulation in comparison to the 3 THIOLA® 100 mg tablets might reflect the absence of dissolution and absorption of tiopronin in the stomach.

A summary of the tiopronin pharmacokinetic parameters is shown below in Table 4.

TABLE 4

Tiopronin Pharmacokinetics - 1 300 mg EC vs. 3 100 mg IR Tablets

| Parameter (units) Statistics | Tiopronin EC 300 mg | | 3 Thiola IR 100 mg | |
|---|---|---|---|---|
| | Replicate 1 (N = 37) | Replicate 2 (N = 33) | Replicate 1 (N = 36) | Replicate 2 (N = 33) |
| $AUC_{0-\infty}$ (hr · ng/mL) | | | | |
| n | 36 | 33 | 36 | 33 |
| Mean ± SD | 40221.93 ± 9433.66 | 40058.53 ± 6904.14 | 41327.97 ± 6734.92 | 40904.67 ± 6792.61 |
| Median | 39410.05 | 40890.32 | 40538.03 | 41491.36 |
| Range | 16848.0-68923.4 | 26931.6-55338.3 | 28161.1-55975.1 | 24833.2-51702.5 |
| Geo Mean | 39082.12 | 39476.70 | 40788.99 | 40324.54 |
| CV (%) | 23.45 | 17.24 | 16.30 | 16.61 |
| $AUC_{0-t}$ (hr · ng/mL) | | | | |
| n | 37 | 33 | 36 | 33 |
| Mean ± SD | 32591.34 ± 8379.83 | 32790.25 ± 4945.68 | 34886.89 ± 5746.59 | 33942.60 ± 5412.95 |
| Median | 32585.93 | 34025.67 | 35252.80 | 33993.70 |
| Range | 9670.7-46781.8 | 23506.6-42894.8 | 23195.9-48094.1 | 20738.3-41637.5 |
| Geo Mean | 31242.33 | 32416.13 | 34428.00 | 33495.16 |
| CV (%) | 25.71 | 15.08 | 16.47 | 15.95 |

TABLE 4-continued

Tiopronin Pharmacokinetics - 1 300 mg EC vs. 3 100 mg IR Tablets

| | Tiopronin EC 300 mg | | 3 Thiola IR 100 mg | |
|---|---|---|---|---|
| Parameter (units) Statistics | Replicate 1 (N = 37) | Replicate 2 (N = 33) | Replicate 1 (N = 36) | Replicate 2 (N = 33) |
| $C_{max}$ (ng/mL) | | | | |
| n | 37 | 33 | 36 | 33 |
| Mean ± SD | 6423.78 ± 2117.90 | 6563.64 ± 1771.13 | 8125.83 ± 1708.07 | 8098.48 ± 1772.50 |
| Median | 6340.00 | 6350.00 | 7985.00 | 7880.00 |
| Range | 1670.0-10900.0 | 3760.0-10900.0 | 5360.0-11700.0 | 5150.0-12400.0 |
| Geo Mean | 6044.13 | 6341.61 | 7951.45 | 7908.03 |
| CV (%) | 32.97 | 26.98 | 21.02 | 21.89 |
| Kel (1/hr) | | | | |
| n | 36 | 33 | 36 | 33 |
| Mean ± SD | 0.01726 ± 0.00393 | 0.01611 ± 0.00384 | 0.01734 ± 0.00373 | 0.01619 ± 0.00254 |
| Median | 0.01741 | 0.01614 | 0.01657 | 0.01571 |
| Range | 0.0087-0.0293 | 0.0060-0.0278 | 0.0085-0.0271 | 0.0107-0.0222 |
| Geo Mean | 0.01680 | 0.01563 | 0.01697 | 0.01600 |
| CV (%) | 22.77889 | 23.86003 | 21.48264 | 15.71506 |
| $t_{1/2}$ (hr) | | | | |
| n | 36 | 33 | 36 | 33 |
| Mean ± SD | 42.49 ± 11.28 | 46.10 ± 15.38 | 41.74 ± 9.29 | 43.84 ± 6.95 |
| Median | 39.80 | 42.95 | 41.84 | 44.11 |
| Range | 23.6-79.5 | 24.9-116.3 | 25.6-81.2 | 31.3-64.6 |
| CV (%) | 26.55 | 33.36 | 22.26 | 15.85 |
| $T_{max}$ (hr) | | | | |
| n | 37 | 33 | 36 | 33 |
| Mean ± SD | 2.84 ± 0.97 | 2.88 ± 0.81 | 1.19 ± 0.35 | 1.18 ± 0.27 |
| Median | 3.00 | 3.00 | 1.05 | 1.00 |
| Range | 1.0-6.0 | 1.5-4.1 | 0.5-2.1 | 1.0-2.0 |
| CV (%) | 34.23 | 28.25 | 29.56 | 23.02 |

The total tiopronin mean plasma exposure did not differ between the 2 replicate doses for the enteric coated tiopronin 300 mg tablets of Example 2 and the 3 THIOLA® IR 100 mg tablets as measured by $C_{max}$, $AUC_{0-t}$, and $AUC_{0-\infty}$. The mean Kel are also similar for both the enteric coated tiopronin 300 mg tablets of Example 2 and the 3 THIOLA® IR 100 mg tablets. The mean $t_{1/2}$ is also similar between the enteric coated tiopronin 300 mg tablets of Example 2 and the 3 THIOLA® IR 100 mg tablets. The similarity in these values for both formulations indicates that tiopronin disposition kinetics (distribution and elimination) did not change in the enteric coated formulation.

As expected, based on the results of Example 2 above, the $T_{max}$ was extended for subjects treated with the enteric coated tiopronin 300 mg tablets by approximately 2 hours compared to the 3 THIOLA® IR 100 mg tablets. The extended $T_{max}$ is consistent with the delay in tiopronin absorption due to stomach transit time (0.5 hours to 1.0 hour) and the observed slow absorption rate as shown in FIG. 6.

The enteric coated tiopronin 300 mg tablet formulation and the 3 THIOLA® 100 mg tablet formulations were bioequivalent for tiopronin exposure ($AUC_{0-t}$ and $AUC_{0-\infty}$). However, the enteric coated tiopronin 300 mg tablets formulation attained <80% of peak exposure ($C_{max}$) of the 3 THIOLA® 100 mg formulation. As designed, the EC dosage showed a delayed absorption profile with an approximately 0.5-hour to 1-hour lag. This indicated transit out of the stomach into the intestine before dissolution and absorption of the dose. Exposure (AUC) is clinically more relevant for efficacy than $C_{max}$ for the following reasons: the mechanism of action of tiopronin; the therapeutic objective to decrease cystine levels over a 24-hour period; and THIOLA® is dosed to effect.

EXAMPLE 4

Next, various lots of tiopronin tablets were placed in solutions of either 0.1 N hydrochloric acid (HCl) or phosphate buffered saline (PBS) having a pH of 6.8. The 100 milligram and 300 milligram enteric coated tablets were placed in the HCl solution for 2 hours and the PBS solution for 45 minutes. The 100 milligram immediate release tablets were placed in the HCl solution for 45 minutes. The % dissolution of each in the various solutions is shown below in Table 5.

TABLE 5

Dissolution of Enteric Coated and Immediate Release Tiopronin

| Tiopronin Tablet (Lot) | Dissolution in HCl (%) | Dissolution in PBS (%) |
|---|---|---|
| 100 mg Enteric Coated (1) | 1.3 | 99.1 |
| 100 mg Enteric Coated (2) | 0.6 | 98.8 |
| 100 mg Enteric Coated (3) | 0.2 | 96.0 |
| 300 mg Enteric Coated (4) | 3.3 | 92.2 |
| 300 mg Enteric Coated (5) | 1.5 | 76.5 |
| 300 mg Enteric Coated (6) | 0.6 | 75.4 |
| 300 mg Enteric Coated (7) | 1.5 | 85.0 |
| 300 mg Enteric Coated (8) | 4.8 | 86.6 |
| 100 mg Immediate Release (9) | 97 | — |
| 100 mg Immediate Release (10) | 93 | — |
| 100 mg Immediate Release (11) | 97 | — |

TABLE 5-continued

Dissolution of Enteric Coated and Immediate Release Tiopronin

| Tiopronin Tablet (Lot) | Dissolution in HCl (%) | Dissolution in PBS (%) |
|---|---|---|
| 100 mg Immediate Release (12) | 94 | — |
| 100 mg Immediate Release (13) | 96 | — |
| 100 mg Immediate Release (14) | 96 | — |

As shown above in Table 5, the enteric coated tiopronin tablets, in either the 100 mg or 300 mg dosage form, exhibited low levels of dissolution in the HCl solution, which mimics the pH of the stomach. On the other hand, the enteric coated tiopronin tablets, in either the 100 mg or 300 mg dosage form, exhibited high levels of dissolution in the PBS solution, which was not nearly as acidic. Meanwhile, the immediate release tiopronin tablets exhibited high levels of dissolution in the acidic HCl solution. This indicates that the enteric coated tablets could exhibit delayed release characteristics since the enteric coated exhibit very low levels of dissolution in the acidic solution, which means that subjects taking the enteric coated tablets could exhibit reduced side effects, such as nausea, that are thought to be caused by the dissolution of the immediate release tablets in the stomach.

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

The invention claimed is:

1. A method for treating cystinuria in a patient in need thereof comprising orally administering to said patient with food a solid pharmaceutical composition comprising:
    a core comprising:
        tiopronin in an amount ranging from 35 to 75 weight percent based on the total weight of the solid pharmaceutical composition ("total wt. %"),
        a diluent in an amount ranging from 10 to 50 total wt. %,
        a binder in an amount ranging from 0.25 to 3 total wt. %,
        a disintegrant in an amount ranging from 1 to 10 total wt. %, and
        a lubricant in an amount ranging from 0.25 to 3 total wt. %;
    an inner coating surrounding the core, wherein the inner coating does not affect the release profile of tiopronin from the solid pharmaceutical composition and comprises a water soluble cellulose-based polymer in an amount ranging from 0.5 to 10 total wt. %; and
    an outer coating surrounding the inner coating, wherein the outer coating comprises:
        an enteric polymer in an amount ranging from 0.25 to 6 total wt. %, wherein the enteric polymer prevents disintegration of the solid pharmaceutical composition in the stomach,
        an anti-tacking agent in an amount ranging from 0.1 to 4 total wt. %, and
        a plasticizer in an amount ranging from 0.025 to 1 total wt. %;
    wherein after oral administration of the solid pharmaceutical composition the mean fed state $C_{max}$ of tiopronin is at least 70% of the mean 12-hour fasted state $C_{max}$ of tiopronin,
    and wherein the solid pharmaceutical composition provides a delay in absorption of tiopronin following oral administration to provide for transit out of the stomach and into the intestine before dissolution, and the solid pharmaceutical composition exhibits at least 75% dissolution after 45 minutes in PBS at pH 6.8.

2. The method of claim 1, wherein after oral administration of the solid pharmaceutical composition the mean fed state $C_{max}$ of tiopronin is at least 75% of the mean 12-hour fasted state $C_{max}$ of tiopronin.

3. The method of claim 1, wherein after oral administration of the solid pharmaceutical composition the mean fed state $C_{max}$ of tiopronin is at least 80% of the mean 12-hour fasted state $C_{max}$ of tiopronin.

4. The method of claim 1, wherein after oral administration of the solid pharmaceutical composition the mean fed state $C_{max}$ of tiopronin ranges from 85% to 95% of the mean 12-hour fasted state $C_{max}$ of tiopronin.

5. The method of claim 1, wherein the core comprises tiopronin in an amount ranging from 40 to 70 total wt. %.

6. The method of claim 1, wherein the core comprises tiopronin in an amount ranging from 50 to 70 total wt. %.

* * * * *